(12) United States Patent
Sakuta et al.

(10) Patent No.: US 11,160,748 B2
(45) Date of Patent: Nov. 2, 2021

(54) NON-RINSE-OFF HAIR PROTECTIVE COSMETIC

(71) Applicant: SHIN-ETSU CHEMICAL CO., LTD., Tokyo (JP)

(72) Inventors: Koji Sakuta, Annaka (JP); Takuya Abe, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/754,155

(22) PCT Filed: Oct. 18, 2018

(86) PCT No.: PCT/JP2018/038787
§ 371 (c)(1),
(2) Date: Apr. 7, 2020

(87) PCT Pub. No.: WO2019/087793
PCT Pub. Date: May 9, 2019

(65) Prior Publication Data
US 2020/0337984 A1    Oct. 29, 2020

(30) Foreign Application Priority Data

Nov. 2, 2017  (JP) .............................. JP2017-212499

(51) Int. Cl.
*A61K 8/893* (2006.01)
*A61K 8/34* (2006.01)
*A61Q 5/12* (2006.01)

(52) U.S. Cl.
CPC ................ *A61K 8/893* (2013.01); *A61K 8/34* (2013.01); *A61K 8/345* (2013.01); *A61Q 5/12* (2013.01)

(58) Field of Classification Search
CPC .......... A61K 8/893; A61K 8/34; A61K 8/345; A61Q 5/12
See application file for complete search history.

(56) References Cited

U.S. PATENT DOCUMENTS

| 9,975,999 B2* | 5/2018 | Tamura ................. A61Q 15/00 |
| 2010/0112017 A1 | 5/2010 | Mizutani et al. |
| 2011/0070173 A1 | 3/2011 | Yoshida et al. |
| 2015/0216790 A1 | 8/2015 | Feng et al. |
| 2019/0023850 A1 | 1/2019 | Takada et al. |

FOREIGN PATENT DOCUMENTS

| EP | 3404068 A1 | 11/2018 |
| JP | H05-004907 A | 1/1993 |
| JP | H05-085918 A | 4/1993 |
| JP | H05-246824 A | 9/1993 |
| JP | 2004-217816 A | 8/2004 |
| JP | 2010-095466 A | 4/2010 |
| JP | 2016-128538 A | 7/2016 |
| JP | 2017-125139 A | 7/2017 |
| WO | 2004/062631 A1 | 7/2004 |
| WO | 2008/032883 A2 | 3/2008 |
| WO | 2014/058887 A1 | 4/2014 |

OTHER PUBLICATIONS

Jan. 8, 2019 International Search Report issued in International Patent Application No. PCT/JP2018/038787.
May 5, 2020 International Preliminary Report on Patentability issued in International Patent Application No. PCT/JP2018/038787.
Nov. 24, 2020 Office Action issued in Japanese Patent Application No. 2017-212499.
May 6, 2021 Office Action issued in Japanese Patent Application No. 2017-212499.
Jul. 20, 2021 Extended European Search Report issued in European Patent Application No. 18873822.3.

* cited by examiner

*Primary Examiner* — Shirley V Gembeh
(74) *Attorney, Agent, or Firm* — Oliff PLC

(57) ABSTRACT

A non-rinse-off hair protective cosmetic including a polyoxyalkylene-modified organopolysiloxane compound which has: a terminal to which a siloxane chain having a polyoxyalkylene group shown by a formula (1) is bonded; 50 or more structural units shown by a formula (2) per molecule; a viscosity of 50,000 mPa·s or more at 25° C.; and an HLB of 1 to 7, where each $R^1$ represents an alkyl group or a phenyl group; A represents a monovalent group having a polyoxyalkylene group shown by a formula (3) or (4). Thus, a non-rinse-off hair protective cosmetic excellent in hair protection performance, resistant to water, but easily removable with a shampoo or the like after use.

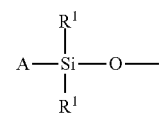

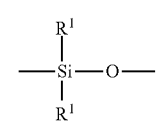

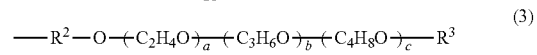

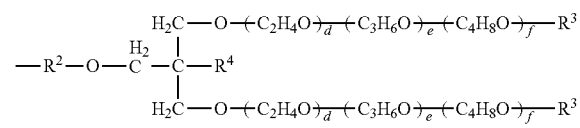

2 Claims, 3 Drawing Sheets

NON-RINSE-OFF HAIR PROTECTIVE COSMETIC

TECHNICAL FIELD

The present invention relates to a non-rinse-off hair protective cosmetic, particularly a non-rinse-off hair protective cosmetic for protecting hair from damage due to friction by brushing and so on and damage due to heat of a dryer.

BACKGROUND ART

To provide hair with glossiness and to smoothly run fingers or a comb through the hair, silicone-blended shampoos have been used conventionally. Moreover, to impart conditioning effect, comparatively highly viscous silicones or gum-like highly viscous silicones have been blended into rinsing liquids and conditioners. Nevertheless, when silicone components blended into shampoos, rinsing liquids, and conditioners are water-soluble silicones such as polyether-modified silicone, these silicone components are washed off during rinsing. Additionally, when dimethyl silicones and amino-modified silicones are blended, a large portion of each component is washed off, and only a small portion in the formulation remains on hair.

Non-rinse-off hair cosmetics include hair oil, hair spray, hair cream hair mousse, hair wax, split hair-coating agent, etc. To enhance the hair protecting effect, highly viscous to gum like dimethyl silicones and amino-modified silicones are blended in some cases (Patent Documents 1, 2, 3).

However, when highly viscous to gum-like silicones having high water repellency are blended in shampoo, it is hard to wash off the silicones. After the repetitive use, the silicones accumulate on hair and impair the hair volume. Moreover, in a case of a cosmetic product to be applied to hair by hand, there is such a problem that even if the hand is washed with soap after the use, the cosmetic is not sufficiently washed down.

Meanwhile, healthy hair is hydrophobic because the surface is covered with the cuticle. However, hair damaged by bleaching or salt water in the sea (what is called damaged hair) has the cuticle deteriorated or peeled at the damaged portion. It is known that such damaged hair is hydrophilic. Even when a hydrophobic, highly-viscous silicone is applied to such hair, the hair surface cannot be protected uniformly.

Conventional polyether-modified silicones having high polyoxyethylene polymerization degree have high hydrophilicity even in the solid phase and are easily washed off, but also flow off by sweat or rain. Patent Document 4 discloses a hair cosmetic containing a combination of a highly viscous dimethylpolysiloxane and a highly viscous polyether-modified silicone compatible with decamethylcyclopentasiloxane, which make it possible to impart favorable smoothness in both drying and wetting states. However, in this case also, the cosmetic such as a shampoo will be supposedly used after rinsing, and it cannot be said that the attachment efficiency to hair is high.

Similarly, Patent Documents 5, 6 also disclose methods utilizing highly viscous polyether-modified silicone as emulsion. Patent Document 5 suggests that the silicone is utilizable for cosmetic usage, too. However, these are methods utilizing emulsion, but are not applied to a non-rinse type hair cosmetic, and a cosmetic excellent in hair protecting performance is not suggested, either.

CITATION LIST

Patent Literature

Patent Document 1: Japanese Patent Laid-Open Publication (Kokai) No. H5-4907

Patent Document 2: Japanese Patent Laid-Open Publication (Kokai) No. H5-85918

Patent Document 3: Japanese Patent Laid-Open Publication (Kokai) No. H5-246824

Patent Document 4: Japanese Patent Laid-Open Publication (Kokai) No. 2004-217816

Patent Document 5: Japanese Patent Laid-Open Publication (Kokai) No. 2016-128538

Patent Document 6: Japanese Patent Laid-Open Publication (Kokai) No. 2017-125139

SUMMARY OF INVENTION

Technical Problem

The present invention has been made in view of the above-described circumstances. An object of the present invention is to provide a non-rinse-off hair protective cosmetic which is excellent in hair protection performance and resistant to water but easily removable with a shampoo or the like after use.

Solution to Problem

To achieve the object, the present invention provides a non-rinse-off hair protective cosmetic comprising a polyoxyalkylene-modified organopolysiloxane compound which has:

a terminal to which a siloxane chain having a polyoxyalkylene group shown by the following general formula (1) is bonded;

50 or more structural units shown by the following general formula (2) per molecule;

a viscosity of 50,000 mPa·s or more at 25 °C; and an HLB of 1.0 to 7.0, wherein each $R^1$ independently represents an alkyl group having 1 to 10 carbon atoms or a phenyl group; and A represents a monovalent group having a polyoxyalkylene group shown by the following general formula (3) or (4), wherein $R^2$ represents a divalent hydrocarbon group having 2 to 10 carbon atoms; $R^3$ represents a hydrogen atom or a group selected from an alkyl group having 1 to 10 carbon atoms and an acyl group; $R^4$ represents a hydrogen atom or an alkyl group having 1 to 5 carbon atoms; 'a_ is a number of 10 to 150, 'b_ is a number of 0 to 75, and 'c_ is a number of 0 to 75, satisfying that a/(a+b+c) is 0.5 to 0.9; and 'd_ is a number of 5 to 100, 'e_ is a number of 0 to 50, and 'f_ is a number of 0 to 50, satisfying that d/(d+e+f) is 0.5 to 0.9.

Such a non-rinse-off hair protective cosmetic incorporating a polyoxyalkylene group-containing organopolysiloxane with a certain structure is thus excellent in adhesion to hair and can uniformly protect the hair cuticle layer. Moreover, the hair protective cosmetic does not flow off by sweat, rain, or the like, but is easily removable by shampoo.

More preferably, in this case, the inventive non-rinse-off hair protective cosmetic comprises:

(A) 100 parts by mass of the polyoxyalkylene-modified organopolysiloxane compound;
(B) 50 to 400 parts by mass of a water-soluble monohydric alcohol or polyhydric alcohol; and
(C) 100 to 1000 parts by mass of water,
wherein the non-rinse-off hair protective cosmetic does not contain an emulsifier.

Such a non-rinse-off hair protective cosmetic can be a transparent homogeneous solution even without a nonionic emulsifier, an anionic emulsifier, a cationic emulsifier, or an amphoteric emulsifier.

Advantageous Effects of Invention

The inventive non-rinse-off hair protective cosmetic is excellent in adhesion to hair, and the protected hair is excellent in smoothness. Accordingly, the inventive cosmetic is capable of preventing damage due to friction by brushing and so on and damage due to heat of a dryer, and is also effective in split-hair prevention.

Additionally, when the inventive non-rinse-off hair protective cosmetic is put on the palm and then applied to hair, the protective ingredient left on the palm can be easily removed by washing with a soap. Moreover, after the application, the ingredient has water resistance and does not flow off by sweat or rain, but can be washed off by shampoo after use. Hence, the protective ingredient does not accumulate on hair even after the repetitive use.

Further, because favorable adhesions to not only healthy hair but also damaged hair are exhibited, the inventive cosmetic is useful as a hair protective cosmetic excellent in functionality and pleasant to use.

DESCRIPTION OF EMBODIMENTS

The present inventors have diligently investigated to achieve the foregoing object and consequently found that when a polyoxyalkylene-modified silicone having a certain polyoxyalkylene group at a molecular terminal and a high viscosity and a relatively low HLB within a certain viscosity range and a certain HLB range is used as a coating agent, a non-rinse-off hair protective cosmetic is obtained which has excellent adhesion to hair and excellent water resistance, and which can be easily washed off after use and consequently does not accumulate. This finding has led to the completion of the present invention.

Specifically, the present invention is a non-rinse-off hair protective cosmetic comprising a polyoxyalkylene-modified organopolysiloxane compound which has:

a terminal to which a siloxane chain having a polyoxyalkylene group shown by the following general formula (1) is bonded;
50 or more structural units shown by the following general formula (2) per molecule;
a viscosity of 50,000 mPa·s or more at 25 °C; and
an HLB of 1.0 to 7.0.

wherein each $R^1$ independently represents an alkyl group having 1 to 10 carbon atoms or a phenyl group; and A represents a monovalent group having a polyoxyalkylene group shown by the following general formula (3) or (4), wherein $R^2$ represents a divalent hydrocarbon group having 2 to 10 carbon atoms; $R^3$ represents a hydrogen atom or a group selected from an alkyl group having 1 to 10 carbon atoms and an acyl group; $R^4$ represents a hydrogen atom or an alkyl group having 1 to 5 carbon atoms; 'a_ is a number of 10 to 150, 'b_ is a number of 0 to 75, and 'c_ is a number of 0 to 75, satisfying that a/(a+b+c) is 0.5 to 0.9; and 'd_ is a number of 5 to 100, 'e_ is a number of 0 to 50, and 'f_ is a number of 0 to 50, satisfying that d/(d+e+f) is 0.5 to 0.9.

The number of structural units of the general formula (2) in one molecule is 50 or more, and the upper limit is preferably 1000. More preferably, the number is 60 or more, and the upper limit is 500.

The viscosity is 50,000 mPa·s or more, and as the upper limit, the polyoxyalkylene-modified organopolysiloxane compound may be semi-solid with no flowability. If the viscosity is less than 50,000 mPa·s, the adhesion to hair is lowered. The viscosity is preferably 100,000 mPa·s or more, further preferably 200,000 mPa·s or more. This viscosity is a viscosity at 25 °C which is measured with a rotary viscometer (manufactured by Toki Sangyo Co., Ltd., model TVB-10 viscometer).

In the present invention, the HLB of the polyoxyalkylene-modified organopolysiloxane compound is a numerical value obtained from the following calculation formula, and ranges from 1.0 to 7.0.

$$HLB = \frac{\text{Mass of Polyoxyethylene Unit in Polyoxyalkylene Modified Organopolysiloxane Compound}}{\text{Molecular Weight of Polyoxyalkylene Modified Organopolysiloxane Compound}} \times 20$$

If the HLB is less than 1.0, the washability by shampoo is insufficient. If the HLB is more than 7.0, the water resistance is lowered. The HLB is preferably 2.0 to 7.0, more preferably 2.0 to 6.0.

$R^1$'s each independently represent an alkyl group having 1 to 10 carbon atoms or a phenyl group. The alkyl group having 1 to 10 carbon atoms may be linear, branched, or cyclic, and is preferably a linear alkyl group. Specific examples of $R^1$ include methyl, ethyl, propyl, butyl, pentyl, hexyl, heptyl, octyl, nonyl, and decyl groups. $R^1$ is preferably a methyl group, an ethyl group, or a phenyl group.

$R^2$'s each represent a divalent hydrocarbon group having 2 to 10 carbon atoms. Specific examples thereof include a phenylenepropylene group, and linear or branched alkylene groups such as ethylene, propylene, trimethylene, n-butylene, isobutylene, s-butylene, n-octylene, 2-ethylhexylene, and n-decylene groups. Preferably, $R^2$ is a propylene, n-butylene, or isobutylene group.

$R^3$'s each represent a hydrogen atom or a group selected from an alkyl group having 1 to 10 carbon atoms and an acyl group. Specific examples of the alkyl group include methyl, ethyl, propyl, butyl, pentyl, hexyl, heptyl, octyl, nonyl, and decyl groups. Specific examples of the acyl group include an acetyl group, a propionyl group, etc. $R^3$ is preferably a hydrogen atom a methyl group, an ethyl group, or an acetyl group.

$R^4$ is a hydrogen atom or an alkyl group having 1 to 5 carbon atoms. Specific examples of the alkyl group include methyl, ethyl, propyl, butyl, pentyl groups, etc. Preferably, $R^4$ is a hydrogen atom a methyl group, or an ethyl group.

'a_ is a number of 10 to 150. 'b_ is a number of 0 to 75. 'c_ is a number of 0 to 75. a/(a+b+c) is 0.5 to 0.9. If a/(a+b+c) is less than 0.5, the washability by shampoo is insufficient. If a/(a+b+c) is more than 0.9, the water resistance is lowered. Preferably, 'a_ is a number of 10 to 100, 'b_ is a number of 0 to 50, and 'c_ is a number of 0 to 50, satisfying that a/(a+b+c) is 0.6 to 0.85. Additionally, each unit 'a_, 'b_, and 'c_ may be either a block copolymer or a random copolymer.

Each 'd_ is independently a number of 5 to 100. Each 'e_ is independently a number of 0 to 50. Each 'f_ is independently a number of 0 to 50. d/(d+e+f) is 0.5 to 0.9. If d/(d+e+f) is less than 0.5, the washability by shampoo is insufficient. If d/(d+e+f) is more than 0.9, the water resistance is lowered. Preferably, 'd_ is a number of 5 to 50, 'e_ is a number of 0 to 25, and 'f_ is a number of 0 to 25, satisfying that d/(d+e+f) is 0.6 to 0.85. Additionally, each unit 'd_, 'e_, and 'f_ may be either a block copolymer or a random copolymer.

The polyoxyalkylene-modified organopolysiloxane of the present invention may contain, besides a compound (the following general formula (5)) composed of the structural unit of the general formula (1) and the structural units of the general formula (2), ones containing a branched structural unit of a $R^1SiO_{(3/2)}$ unit (for example, the following general formula (6)) or a $SiO_2$ unit (for example, the following general formula (7)).

In the formula, A and $R^1$ are as defined above, and $x^1$ is 50 or more.

In the formula, A and $R^1$ are as defined above, and $x^1+x^2$ is 50 or more.

In the formula, A and $R^1$ are as defined above, and $x^3+x^4+x^5$ is 50 or more.

In the above formula, 'y_ and 'z_ each preferably represent a number of 1 to 5. 'y_ and 'z_ are preferably 5 or less because there are not too many branched structural units to be crosslinked. 'y_ and 'z_ are more preferably 1 to 3.

The polyoxyalkylene-modified organopolysiloxane compound used in the present invention can be obtained according to a conventional method of addition reaction between an organopolysiloxane having a Si—H group at a molecular terminal and a polyoxyalkylene compound having a terminal unsaturated group.

Specifically, description will be given of an example in which a polyoxyalkylene-modified diorganopolysiloxane compound shown by the general formula (5) is produced. This compound can be obtained by reaction of a diorganohydrogenpolysiloxane shown by the following general formula (8) and a polyoxyalkylene compound containing a terminal unsaturated group shown by the following general formula (9) or (10).

(8)

(9)

(10)

In the formulae, each $R^1$, $R^3$, $R^4$, 'a_, 'b_, 'c_, 'd_, 'e_, 'f_, and $x^1$ are as defined above. $R^6$ represents hydrogen or a methyl group. $R^5$ represents a divalent hydrocarbon group having 0 to 8 carbon atoms when $R^6$ is hydrogen, and represents a divalent hydrocarbon group having 0 to 7 carbon atoms when $R^6$ is a methyl group.

The polyoxyalkylene-modified organopolysiloxane compound obtained by addition reaction may be subjected to a deodorant process according to a known method such as hydrolysis of the unreacted unsaturated terminal group with acidic aqueous solution and hydrogenation thereof.

The inventive non-rinse-off hair protective cosmetic is used without rinsing off after directly applied to hair, and protects the cuticle layer by the application to any of the whole surface of hair or a portion thereof. The inventive hair protective cosmetic is excellent in adhesion to hair and the protected hair is excellent in smoothness. Thus, damage due to friction by brushing and so on and damage due to heat of a dryer can be prevented, and split hair can also be prevented effectively. Moreover, the hair protective cosmetic does not flow off by sweat, rain, or the like, but is easily removable by shampoo.

Preferably, the inventive non-rinse-off hair protective cosmetic contains, based on 100 parts by mass of the polyoxyalkylene-modified organopolysiloxane (a component (A)), 50 to 400 parts by mass of a component (B) that is a water soluble monohydric alcohol or polyhydric alcohol, and 100 to 1000 parts by mass of a component (C) that is water, but does not contain an emulsifier. Such a hair protective cosmetic can be a transparent homogeneous solution without a nonionic emulsifier, an anionic emulsifier, a cationic emulsifier, or an amphoteric emulsifier.

Note that, without the water of the component (C), a transparent homogeneous solution can be formed using only the components (A) and (B). Nevertheless, to improve the pleasantness of use, the above composition ratio is preferable.

With 50 parts by mass or more of the component (B), there is no fear that the transparency of the composition is impaired. With 400 parts by mass or less, there is no fear that the adhesion to hair is lowered. Thus, this range is preferable. Further preferably, the range is 50 to 300 parts by mass.

With 100 parts by mass or more of the component (C), the refreshing feeling upon application to hair is improved. With 1000 parts by mass or less, there is no fear that the transparency of the composition is impaired. Thus, this range is preferable. Further preferably, the range is 120 to 800 parts by mass.

Specific examples of the component (B) include lower alcohols such as ethanol and 2-propanol; and polyhydric alcohols such as propylene glycol, butylene glycol, dibutylene glycol, glycerin, and diglycerin.

A preferable mode of the present invention is as described above but is not limited to the hair protective cosmetic which contains, based on 100 parts by mass of the component (A) polyoxyalkylene-modified organopolysiloxane, 50 to 400 parts by mass of the component (B) water-soluble monohydric alcohol or polyhydric alcohol, and 100 to 1000 parts by mass of the component (C) water, but which does not contain an emulsifier. When the inventive non-rinse-off hair protective cosmetic is prepared, known component(s) for cosmetics may be blended.

Specific examples thereof include oils such as silicone oil, hydrocarbon oil, and ester oil; higher alcohols such as lauryl alcohol, myristyl alcohol, and stearyl alcohol; salts such as inorganic salts, organic salts, and amine hydrochloride; plant polymers such as arabia gum guar gum and starch; microorganism-derived polymers such as xanthan gum and dextrin; cellulose polymers such as methyl cellulose, methyl hydroxypropyl cellulose, and carboxymethyl cellulose; vinyl polymers such as carboxyvinyl polymers; acrylic polymers such as sodium polyacrylate and polyacryl amide; inorganic polymers such as bentonite, montmorillonite, and silicic anhydride; water-soluble synthetic polymers such as polyvinyl alcohol and polyoxyethylene; powders such as inorganic powder, organic powder, metal salt powder, colored pigment, pearl pigment, and natural pigment; and other components used for ordinal cosmetics, such as an ultraviolet light protective agent, an antiperspirant, an oil-soluble gelation agent, a moisturizer, an antioxidant, a fragrance, an antiseptic, a pH adjuster, a cooling agent, a skin-whitening agent, and vitamins.

Additionally, it is also possible to blend what is called an emulsifier generally used for cosmetic usage, for example, polyether-modified silicones (low viscosity products) known as nonionic emulsifiers, nonionic emulsifiers other than polyether-modified silicones, an anionic emulsifiers, cationic emulsifiers, and amphoteric emulsifiers.

EXAMPLE

Hereinafter, the present invention will be more specifically described by showing Examples and Comparative Examples, but the present invention is not limited to the following Examples.

Synthesis Example 1

Into a flask, 753.4 g of methyl hydrogen polysiloxane shown by the following formula (11), 331.4 g of a polyoxyalkylene compound shown by the following formula (12), and 1085.0 g of 2-propanol were introduced. To these, 0.11 g of Karstedt catalyst (platinum concentration: 3%) and 0.24 g of 10% potassium acetate solution in ethanol were added, and the reaction was carried out at 80 °C for 5 hours. After the reaction, the solvent was removed under reduced pressure to give polyoxyalkylene-modified diorganopolysiloxane shown by the following formula (13) (hereinafter referred to as Compound 1). The calculated HLB value was 4.0, and the viscosity at 25 °C was 844,000 mPa·s.

(11)

(12)

(13)

Synthesis Example 2

679.4 g of methyl hydrogen polysiloxane shown by the following formula (14), 331.4 g of a polyoxyalkylene compound shown by the formula (12), and 1050.0 g of 2-propanol were prepared. To these, 0.11 g of Karstedt catalyst (platinum concentration: 3%) and 0.24 g of 10% potassium acetate solution in ethanol were added to give a polyoxyalkylene-modified diorganopolysiloxane shown by the following formula (15) (hereinafter referred to as Compound 2) as in Synthesis Example 1. The calculated HLB value was 4.2, and the viscosity at 25 °C was 421,000 mPa·s.

(14)

(15)

Synthesis Example 3

297.3 g of methyl hydrogen polysiloxane shown by the following formula (16), 33.1 g of a polyoxyalkylene compound shown by the formula (12), 660.0 g of 2-propanol, 0.03 g of Karstedt catalyst (platinum concentration: 3%), and 0.06 g of 10% potassium acetate solution in ethanol were added together to give a polyoxyalkylene-modified diorganopolysiloxane shown by the following formula (17) (hereinafter referred to as Compound 3) as in Synthesis Example 1. The calculated HLB value was 1.3, and the viscosity at 25 °C was 2,960,000 mPa·s.

(16)

(17)

Synthesis Example 4

150.7 g of methyl hydrogen polysiloxane shown by the following formula (18) ($x^1+x^2=200$), 49.7 g of a polyoxyalkylene compound shown by the formula (12), 300.0 g of 2-propanol, 0.03 g of Karstedt catalyst (platinum concentration: 3%), and 0.06 g of 10% potassium acetate solution in ethanol were added together to give a semi-solid polyoxyalkylene-modified organopolysiloxane shown by the following formula (19) (hereinafter referred to as Compound 4) as in Synthesis Example 1. The calculated HLB value was 3.2.

(18)

(19)

Synthesis Example 5

75.3 g of methyl hydrogen polysiloxane shown by the formula (11), 33.6 g of a polyoxyalkylene compound shown by the following formula (20), 110.0 g of 2-propanol, 0.02 g of Karstedt catalyst (platinum concentration: 3%), and 0.04 g of 10% potassium acetate solution in ethanol were added together to give a polyoxyalkylene-modified diorganopolysiloxane shown by the following formula (21) (hereinafter referred to as Compound 5) as in Synthesis Example 1. The calculated HLB value was 3.9, and the viscosity at 25 °C was 547,000 mPa·s.

Examples 1 to 5

According to compositions shown in Table 1 below, hair protective cosmetics were prepared, and hairs were treated by the following method and observed through electron microscope and photographed.

[Hair Treatment Method (Ordinal Hairs)]
1. About 1.5 g of commercially available hairs (ordinal hairs) were tied on each one end to prepare a hair bundle, and this was observed through electron microscope and photographed (before treatment).
2. The hair bundle was introduced into a vessel containing a protective agent solution (hair protective cosmetic), and was soaked for 5 minutes.
3. The hair bundle was taken out, and the excess liquid attached thereto was wiped out. Then, the hair bundle was dried being hung with the hair ends pointing downward. After drying, the hair bundle was observed through electron microscope and photographed (after treatment).
4. The hair bundle was introduced into a vessel containing water, and washed for 5 minutes with shaking. The excess water drops were wiped out with a towel. Then, the hair bundle was dried being hung with the hair ends pointing downward. After drying, the hair bundle was observed through electron microscope and photographed (after water washing).
5. The hair bundle was introduced into a solution of commercially available non-silicone shampoo, and washed for 5 minutes with shaking. After the shampoo components were rinsed off, the excess water drops were wiped out with a towel, and the hair bundle was dried being hung with the bundled end pointing downward. After drying, the hair bundle was observed through electron microscope and photographed (after shampoo).

[Apparatus used and Observation Conditions]
(Apparatus)
a desk-top scanning electron microscope (manufactured by JEOL Ltd., JCM-6000Plus)
(Conditions)
acceleration voltage: 5.0 kV, magnification: 500-power, 1000-power, pre-treatment: vapor deposition of gold microparticles

[Observation Result Judging Method]
The electron micrographs were judged according to the following criteria.
(After Treatment)
Excellent: uniformly adhered to the whole surface of the hair.
Fair: found partially non-adhered to the hair. Otherwise, found that the adhesion was uneven.
Bad: clearly found not uniformly adhered.
(After Water Washing)
Excellent: remained uniformly adhered to the whole surface of the hair.
Fair: found partially non-adhered to the hair.
Bad: clearly found removed from the hair.
(After Shampoo)
Excellent: clearly removed from the hair, and no protective agent was found remaining.
Fair: a portion of the protective agent was found remaining.
Bad: found not removed from the hair and noticeably remaining.

Table 1 shows the compositions and the evaluation results of the hair protective cosmetics. Note that the composition of each hair protective cosmetic is shown in mass %.

TABLE 1

|  |  | Example 1 | Example 2 | Example 3 | Example 4 | Example 5 |
|---|---|---|---|---|---|---|
| Composition of hair protective cosmetic | Compound 1 | 20 | — | — | — | — |
|  | Compound 2 | — | 20 | — | — | — |
|  | Compound 3 | — | — | 20 | — | — |
|  | Compound 4 | — | — | — | 20 | — |

TABLE 1-continued

|  |  | Example 1 | Example 2 | Example 3 | Example 4 | Example 5 |
|---|---|---|---|---|---|---|
|  | Compound 5 | — | — | — | — | 20 |
|  | Ethanol | 24 | 24 | 24 | 24 | 24 |
|  | Water | 56 | 56 | 56 | 56 | 56 |
| Evaluation | After treatment | Excellent | Excellent | Excellent | Excellent | Excellent |
|  | After water washing | Excellent | Excellent | Excellent | Excellent | Excellent |
|  | After shampoo | Excellent | Excellent | Excellent to Fair | Excellent | Excellent |

Figure 1:
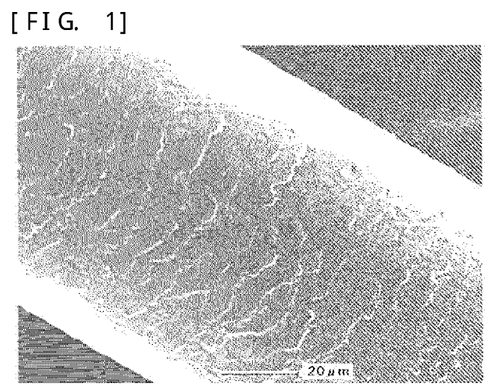
FIG. 1 is an electron micrograph of hair (ordinal hair) before treatment in Example 1.
Figure 2:
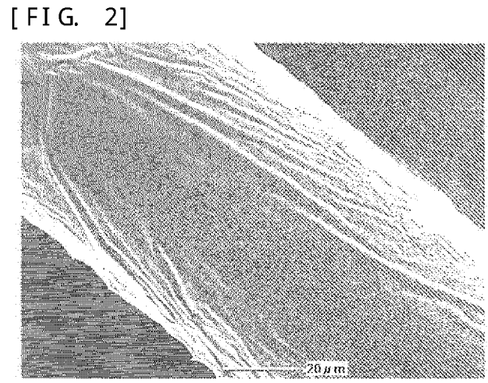
FIG. 2 is an electron micrograph of the hair (ordinal hair) after the treatment in Example 1.
Figure 3:
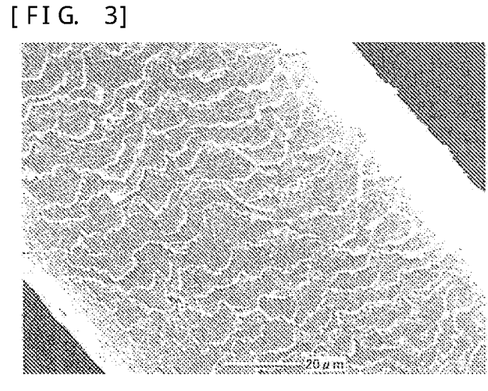
FIG. 3 is an electron micrograph of the hair (ordinal hair) after a shampoo in Example 1.

The electron micrograph observations confirmed the adhesion to the whole surface of the hair after the treatment. Moreover, the hair protective cosmetics were not removed after the water washing, and kept the favorable adhesion. This suggested that the hair protective cosmetics do not flow off by sweat or rain. Further, it was verified that after the shampoo, the hair protective cosmetics were sufficiently removed from the hair surface and did not remain. Note that FIG. 1 shows an electron micrograph (B1000) before the treatment in Example 1, FIG. 2 shows an electron micrograph (B1000) after the treatment in Example 1, and FIG. 3 shows an electron micrograph (B1000) after the shampoo in Example 1.

Examples 6 to 10

According to compositions shown in Table 2 below, hair protective cosmetics were prepared. The treatment was performed therewith by the above-described method, and Table 2 also shows the evaluation results through the electron micrograph observation.

TABLE 2

|  |  | Example 6 | Example 7 | Example 8 | Example 9 | Example 10 |
|---|---|---|---|---|---|---|
| Composition of hair protective cosmetic | Compound 1 | 10 | 30 | 10 | — | — |
|  | Compound 2 | — | — | — | 10 | — |
|  | Compound 5 | — | — | — | — | 10 |
|  | Ethanol | 27 | 21 | — | — | — |
|  | 1,3-BG | — | — | 27 | 27 | 27 |
|  | Water | 63 | 49 | 63 | 63 | 63 |
| Evaluation | After treatment | Excellent | Excellent | Excellent | Excellent | Excellent |
|  | After water washing | Excellent | Excellent | Excellent | Excellent | Excellent |
|  | After shampoo | Excellent | Excellent | Excellent | Excellent | Excellent |

As shown in Table 2, the effects did not change even when the concentration of the polyoxyalkylene-modified silicone was reduced and/or when 1,3-BG (1,3-butylene glycol) was used as polyhydric alcohol.

Comparative Examples 1 to 3

Various highly-polymerized silicone compositions which had been conventionally used as hair protective cosmetics were used to treat hairs as described above. Table 3 shows the evaluation results. Incidentally, since these compositions were not uniformly dispersed in the aqueous alcohol solution, a volatile decamethylcyclopentasiloxane solution was used.

TABLE 3

|  |  | Comparative Example 1 | Comparative Example 2 | Comparative Example 3 |
|---|---|---|---|---|
| Composition of hair protective cosmetic | Highly-polymerized silicone solution*1) | 50 | — | — |
|  | Highly-polymerized silicone solution*2) | — | 50 | — |
|  | Highly-polymerized silicone solution*3) | — | — | 50 |
|  | Decamethylcyclopentasiloxane | 50 | 50 | 50 |
| Evaluation | After treatment | Excellent | Excellent | Excellent |
|  | After water washing | Excellent | Excellent | Excellent |
|  | After shampoo (1st time) | Bad | Bad | Bad |
|  | After shampoo (2nd time) | Bad | Bad | Bad |

*1)composition composed of gum-like dimethylpolysiloxane (25 mass %) having a polymerization degree of 5000 and isononyl isononanoate (75 mass %)
*2)composition composed of gum-like dimethylpolysiloxane (20 mass %) having a polymerization degree of 5000 and decamethylcyclopentasiloxane (80 mass %)
*3)composition composed of dimethylpolysiloxane (30 mass %) having a viscosity of 1,000,000 mPa·s at 25 ėC and dimethylpolysiloxane (70 mass %) having a viscosity of 20 mPa·s As show in Table 3, when the treatment was performed in the same manner with the conventional highly-polymerized silicone solutions, the compositions were uniformly applied after the treatment, and did not fall off even after the water washing. However, it was found that the compositions noticeably remained after the shampoo. Further, even after shampooing was carried out one more time, the remaining did not change.

Comparative Examples 4 to 7

According to compositions shown in Table 4, hair protective cosmetics were prepared. The treatment was performed therewith by the above-described method, and the evaluation results through the electron micrograph observation are shown.

TABLE 4

|  |  | Comparative Example 4 | Comparative Example 5 | Comparative Example 6 | Comparative Example 7 |
|---|---|---|---|---|---|
| Composition of hair protective cosmetic | Polyether-modified silicone 1 | 20 | — | — | — |
|  | Polyether-modified silicone 2 | — | 20 | — | — |
|  | Polyether-modified silicone 3 | — | — | 20 | — |
|  | Polyether-modified silicone 4 | — | — | — | 20 |
|  | Ethanol | 24 | 24 | 24 | 24 |
|  | Water | 56 | 56 | 56 | 56 |
| Evaluation | After treatment | Fair | Fair | Fair | Fair |
|  | After water washing | Fair | Bad | Bad | Fair |
|  | After shampoo | Excellent | — | — | Excellent |

Polyether-modified silicone 1: polyether-modified silicone shown by the following structural formula and having an HLB of 3.9 and a viscosity of 400 mPa·s at 25 °C

Polyether-modified silicone 2: polyether-modified silicone shown by the following structural formula and having an HLB of 6.0 and a viscosity of 1500 mPa·s at 25 °C Polyether-modified silicone 3: polyether-modified silicone shown by the following structural formula and having an HLB of 6.5 and a melting point of 45 °C Polyether-modified silicone 4: polyether-modified silicone shown by the following structural formula and having an HLB of 5.4 and a viscosity of 38,000 mPa·s at 25 °C As shown in Table 4, all resulted in inferior uniform applications after the treatment. In Comparative Examples 5 and 6, the cosmetics were removed from the hairs at the stage after the water washing. In Comparative Examples 4 and 7, the removal was observed at the stage after the shampoo.

Examples 11, 12, Comparative Examples 8, 9

According to compositions shown in Table 5, hair protective cosmetics were prepared, and the effects on bleached Damaged hair 1 and saline-treated Damaged hair 2 were examined. The hair treatment methods were described below.
[Hair Treatment Method (Damaged hairs 1, 2)]
(Damaged Hair 1)
1. A hair bundle was prepared from commercially available hairs (ordinal hairs) as described above, and soaked in a commercially available bleach for 45 minutes.
2. The hair bundle was taken out, sufficiently rinsed, and then the excess water drops were wiped out with a towel. The hair bundle was dried being hung with the hair ends pointing downward. After drying, the hair bundle was observed through electron microscope and photographed (before treatment).
3. The hair bundle was introduced into a vessel containing a protective agent solution (hair protective cosmetic), and was soaked for 5 minutes.
4. The hair bundle was taken out, and the excess liquid attached thereto was wiped out. Then, the hair bundle was dried being hung with the hairs pointing downward. The dried hairs were observed through electron microscope and photographed (after treatment).
5. The hairs were introduced into a solution of commercially available non-silicone shampoo, and washed for 5 minutes with shaking. After the shampoo components were rinsed off, the excess water drops ware wiped out with a towel, and the hair bundle was dried being hung with the bundled end pointing downward. After drying, the hair bundle was observed through electron microscope and photographed (after shampoo).
(Damaged Hair 2)
1. A hair bundle was prepared from commercially available hairs (ordinal hairs) as described above, and soaked in saline with a concentration of 3.5 mass % for 45 minutes.
2. The hair bundle was taken out, sufficiently rinsed, and then the excess water drops were wiped out with a towel. The hair bundle was dried being hung with the hair ends pointing downward. After drying, the hair bundle was observed through electron microscope and photographed (before treatment).
3. The hair bundle was introduced into a vessel containing a protective agent solution (hair protective cosmetic), and was soaked for 5 minutes.
4. The hair bundle was taken out, and the excess liquid attached thereto was wiped out. Then, the hair bundle was dried being hung with the hairs pointing downward. The dried hairs were observed through electron microscope and photographed (after treatment).
5. The hairs were introduced into a solution of commercially available non-silicone shampoo, and washed for 5 minutes with shaking. After the shampoo components were rinsed off, the excess water drops were wiped out with a towel, and the hair bundle was dried being hung with the bundled end pointing downward. After drying, the hair bundle was observed through electron microscope and photographed (after shampoo).

Figure 4:
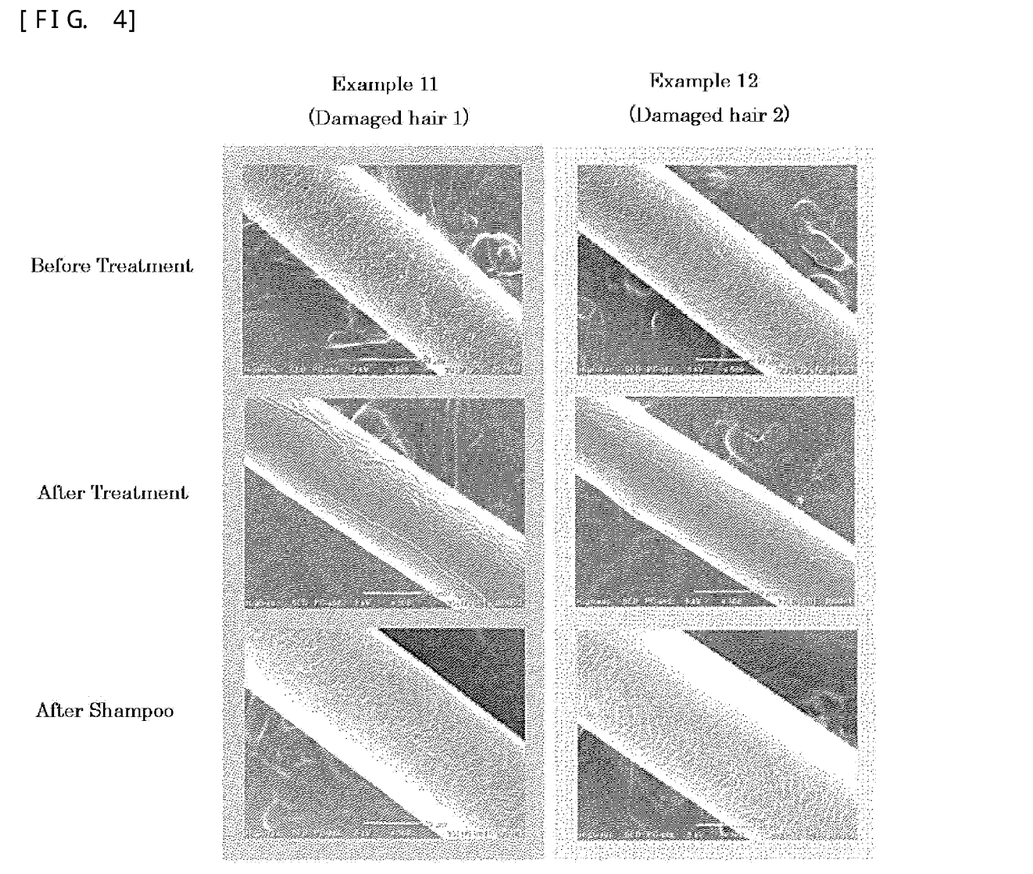
FIG. 4 shows electron micrographs for observing treatment effects on damaged hairs in Examples 11, 12.
Figure 5:
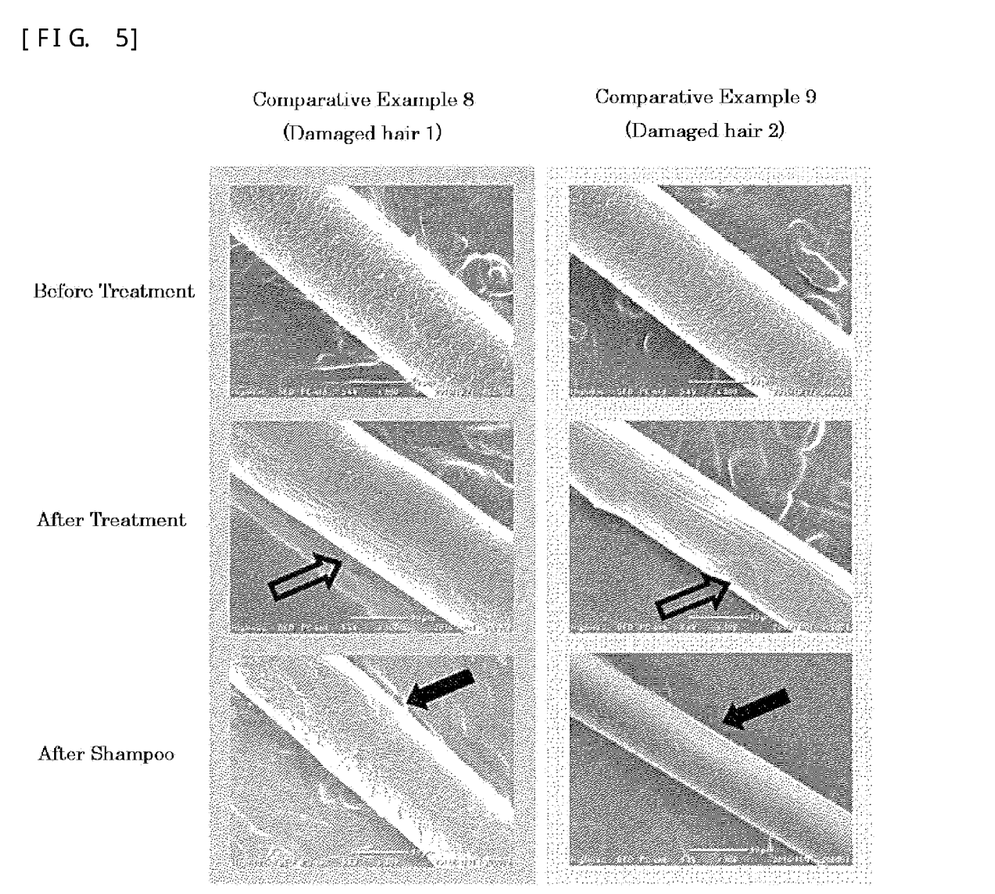
FIG. 5 shows electron micrographs for observing treatment effects on damaged hairs in Comparative Examples 8, 9.

Table 5 shows the evaluation results through the electron micrograph observation. Note that FIG. 4 shows electron micrographs (B500) before the treatment, after the treatment, and after the shampoo in Example 11 (Damaged hair 1) and Example 12 (Damaged hair 2); and FIG. 5 shows electron micrographs (B500) before the treatment, after the treatment, and after the shampoo in Comparative Example 8 (Damaged hair 1) and Comparative Example 9 (Damaged hair 2).

TABLE 5

|  |  | Damaged hair 1 | | Damaged hair 2 | |
| --- | --- | --- | --- | --- | --- |
|  |  | Example 11 | Comparative Example 8 | Example 12 | Comparative Example 9 |
| Composition of hair protective cosmetic | Compound 1 | 20 | — | 20 | — |
|  | Highly-polymerized silicone solution (above *1) | — | 50 | — | 50 |
|  | Decamethylcyclopentasiloxane | — | 50 | — | 50 |
|  | Ethanol | 24 | — | 24 | — |
|  | Water | 56 | — | 56 | — |
| Evaluation | After treatment | Excellent | Fair | Excellent | Fair |
|  | After shampoo | Excellent | Bad | Excellent | Bad |

As a result, the inventive hair protective cosmetics were excellent in adhesion to hair and removability after the shampoo with respect to both Damaged hairs 1 and 2 (Examples 11, 12). Meanwhile, when the highly-polymerized silicone solution was used, the adhesion to hair was insufficient, and the removability after the shampoo was inferior (Comparative Examples 8, 9).

It should be noted that the present invention is not United to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A non-rinse-off hair protective cosmetic comprising a polyoxyalkylene-modified organopolysiloxane compound which is a coating agent and has:
    a terminal to which a siloxane chain having a polyoxyalkylene group shown by the following general formula (1) is bonded;
    50 or more structural units shown by the following general formula (2) per molecule;
    a viscosity of 50,000 mPa·s or more at 25° C.; and
    an HLB of 1.0 to 7.0, wherein each $R^1$ independently represents an alkyl group having 1 to 10 carbon atoms or a phenyl group; and A represents a monovalent group having a polyoxyalkylene group shown by the following general formula (3) or (4), wherein $R^2$ represents a divalent hydrocarbon group having 2 to 10 carbon atoms; $R^3$ represents a hydrogen atom or a group selected from an alkyl group having 1 to 10 carbon atoms and an acyl group; $R^4$ represents a hydrogen atom or an alkyl group having 1 to 5 carbon atoms; "a" is a number of 10 to 150, "b" is a number of 0 to 75, and "c" is a number of 0 to 75, satisfying that a/(a+b+c) is 0.5 to 0.9; and "d" is a number of 5 to 100, "e" is a number of 0 to 50, and "f" is a number of 0 to 50, satisfying that d/(d+e+f) is 0.5 to 0.9.

2. The non-rinse-off hair protective cosmetic according to claim 1, comprising:
    (A) 100 parts by mass of the polyoxyalkylene-modified organopolysiloxane compound;
    (B) 50 to 400 parts by mass of a water-soluble monohydric alcohol or polyhydric alcohol; and
    (C) 100 to 1000 parts by mass of water,
    wherein the non-rinse-off hair protective cosmetic does not contain an emulsifier.

* * * * *